(12) United States Patent
Connolly et al.

(10) Patent No.: US 9,057,112 B2
(45) Date of Patent: *Jun. 16, 2015

(54) USE OF SELECTED LACTIC ACID BACTERIA FOR REDUCING INFANTILE COLIC

(75) Inventors: Eamonn Connolly, Lidingö (SE); Bo Mollstam, Lerum (SE)

(73) Assignee: BIOGAIA AB, Stockholm (SE)

( * ) Notice: Subject to any disclaimer, the term of this patent is extended or adjusted under 35 U.S.C. 154(b) by 1247 days.

This patent is subject to a terminal disclaimer.

(21) Appl. No.: 11/978,417

(22) Filed: Oct. 29, 2007

(65) Prior Publication Data

US 2008/0131414 A1 Jun. 5, 2008

Related U.S. Application Data

(62) Division of application No. 11/446,628, filed on Jun. 5, 2006, now Pat. No. 7,374,924.

(51) Int. Cl.
 *C12N 1/20* (2006.01)
 *C12R 1/225* (2006.01)
 *A61K 31/22* (2006.01)

(52) U.S. Cl.
 CPC ............... *C12R 1/225* (2013.01); *A61K 31/22* (2013.01); *A61K 35/747* (2013.01); *C12N 1/20* (2013.01); *Y10S 435/853* (2013.01)

(58) Field of Classification Search
 CPC . A61K 35/747; A61K 2300/00; A61K 31/22; A61K 38/22; A61K 38/225; A61K 35/74; A61K 31/353; A61K 31/4164; A61K 31/4172; A61K 31/4184; A61K 31/43; A61K 31/496; A61K 31/65; A61K 31/7036; A61K 35/741
 See application file for complete search history.

(56) References Cited

U.S. PATENT DOCUMENTS

| | | | |
|---|---|---|---|
| 4,518,696 A | 5/1985 | Gehrman et al. | |
| 5,439,678 A | 8/1995 | Dobrogosz et al. | |
| 5,458,875 A | 10/1995 | Casas-Perez et al. | |
| 5,534,253 A | 7/1996 | Casas et al. | |
| 5,800,813 A | 9/1998 | Casas | |
| 5,837,238 A | 11/1998 | Casas et al. | |
| 5,849,289 A | 12/1998 | Dobrogosz et al. | |
| 6,036,952 A | 3/2000 | Oh | |
| 6,100,388 A | 8/2000 | Casas et al. | |
| 6,103,227 A | 8/2000 | Wolf et al. | |
| 7,374,924 B2 * | 5/2008 | Connolly et al. | 435/252.9 |
| 2004/0067573 A1 | 4/2004 | Connolly et al. | |
| 2004/0185032 A1 * | 9/2004 | Burrell | 424/93.45 |
| 2004/0208863 A1 | 10/2004 | Versalovic et al. | |

* cited by examiner

*Primary Examiner* — Debbie K Ware
(74) *Attorney, Agent, or Firm* — Lynn E. Barber

(57) ABSTRACT

The invention herein provides certain strains of lactic acid bacteria selected for their capability of promoting production of IL-10 and consequently proliferation of CD4+CD25+ TR cells, for prophylaxis and/or treatment of infant colic, a method of selecting such strains, and products containing such strains.

4 Claims, 2 Drawing Sheets

| | IL-10 production (pg/ml) |
|---|---|
| MRS | |
| ATCC 55730 | 1500 |
| DSM 17938 | 1450 |
| ATCC PTA 4660 | 35 |
| ATCC PTA 4964 | 47 |

USE OF SELECTED LACTIC ACID BACTERIA FOR REDUCING INFANTILE COLIC

CROSS-REFERENCE TO RELATED APPLICATIONS

This is a divisional patent application of U.S. patent application Ser. No. 11/446,628 filed Jun. 5, 2006, now U.S. Pat. No. 7,374,924.

BACKGROUND OF THE INVENTION

1. Field of the Invention

The invention herein provides certain strains of lactic acid bacteria selected for their ability of increasing cytokine IL-10 levels, for prophylaxis and/or treatment of colic, a method of selecting such strains, and products containing such strains.

2. Description of the Related Art

Despite its salience in terms of both prevalence and distress the nature and causes of infantile colic have remained poorly understood. A mother's description of this condition is a baby who has been happy during the day, begins to frown, his face becomes red, he draws up his legs, screams and continues to cry for about 2-20 min after which the attack ends suddenly. Controversy arises even in the terms used to describe the condition. These terms include, "infantile colic", "evening colic" because the pain is mainly confined to evening, and "three months colic" under the pretext that it disappears after about three months from birth (Illingworth R S. Difficulties in breastfeeding. In Ronald S. Ellingworth, ed. The Normal Child. 10th edn. Harcourt (India) Pvt. Ltd. 1997; 39-44). Different authors have used different definitions. The definition of Wessels that colic is paroxysms of crying for three or more hours per days for three days or more per week during a period of at least three weeks, is mostly accepted in the literature (Sondergaard C, Skajaa E, Henriksen T B. Fetal growth and infantile colic. Arch Dis Child Fetal-Neonatal Ed 2000; 83 (1): F44-47). To date, the main possible causative factors has been divided into three groups: psychosocial, gastrointestinal and neuro-developmental disorders.

Psychosocial factors include: variant of normal crying, behavioral effects of atypical parenting, and manifestation of problems in parent-infant interaction.

Gastrointestinal disorders have been implicated in colic because of the infant's leg position and grimacing during a crying spell. The gastrointestinal factors are briefly reviewed below:

Improper feeding techniques like bottle feeding, feeding in a horizontal position and lack of burping post-feeding have been considered as causative factors. Breast-feeding in the first six months has been found to be a sole protective factor. The risk of infantile colic is 1.86 times higher among non-breast fed infants (Saavedra M A, Dacosta J S, Garcias G, Horta B L, Tomasi E, Mendoca R. Infantile colic incidence and associated risk factors: a cohort study. Pediatr (Rio J) 2003; 79(2): 115-122). Lothe et al. showed that colic is from sensitivity to cow's milk whey protein (Lothe L, Lindberg T. Cow's milk whey protein elicits symptoms of infantile colic in colicky formula-fed infants: A double-blind cross over study. Pediatrics 1989; 83: 262).

In a recent study, it was concluded that food hypersensitivity could be defined as causative in only a minority of cases of infantile colic (Hill D J, Hosking C S. Infantile colic and food hypersensitivity. J Pediatr Gastrenterol Nutr 2000; 30 (Suppl): S67-76). Recently Buchanan has shown that a trial of hypoallergenic milk in infantile colic is not supported by enough evidence (Buchanan P. Effectiveness of treatment for infantile colic. Trial of hypoallergenic milk is not supported by strong enough evidence. BMJ 1998; 317(7170): 1451-1452). Babies with infantile colic are thought to be at higher risk of allergic diseases. However, in a recent study, markers of atopy, allergic rhinitis, asthma, wheezing and peak flow variability, are shown to be comparable in infants with or without infantile colic (Castro-Rodriguez J A, Stern D A, Halonen M, Wright A L, Holberg C J et al. Relationship between infantile colic and Asthma/atopy: A prospective study in an unselected population. Pediatrics 2001; 108(4): 878-882).

Lactose malabsorption has been reported by authors based on breath hydrogen tests (Hyams J, Geerstama M, Etienne N, Treem W. Colonic hydrogen production in infants with colic. J Pediatr 1989; 115: 592). No differences have been found in stool hydrogen concentrations between infants with or without infantile colic. However, infants producing higher methane levels have been found to have decreased colic suggesting a role of methane production in its alleviation (Belson A, Shetty A K, Yorgin P D, Bujanover Y, Peled Y, Dar M H, Riaf S. Colonic hydrogen elimination and methane production in infants with and without infantile colic syndrome. Dig Dis Sci 2003; 48(9): 1762-1766).

Gastrointestinal (GIT) hormones such as motilin, vasoactive intestinal peptide have been shown to be abnormally high in babies with colic. Lothe et al. have shown elevated levels from first day of life in babies who later developed colic suggesting an abnormal GIT physiology in infantile colic (Lothe L, Ivassson S A, Ekman R, Lindberg T. Motilin and infantile colic: A prospective study. Acta Pediatr Scand 1990; 79(4): 410-416).

Neuro-developmental disorders that have been put forward suggest that abdominal cramping and colic may be a result of hyperperistalsis. The theory is supported by evidence that the use of anticholinergic agents decreases colic symptoms (Gupta S K. Is colic a gastrointestinal disorder? Curr Opin Pediatr 2002; 14:588-92).

The fact that most infants outgrow colic by four months of age lends support to a neurodevelopmental cause of colic (Barr R G. Colic and crying syndromes in infants. Pediatrics 1998; 102(5 suppl E):1282-6).

A probiotic, by the generally accepted definition, is a live microbial feed supplement which beneficially affects the host animal by improving its intestinal microbial balance. Although originally referring to the supplementation of animal feeds for farm animals, the definition is easily applied to the human situation. The major consumption of probiotics by humans is in the form of dairy-based foods containing intestinal species of lactobacilli and bifidobacteria. It is implicit in the definition that consumption of the probiotic affects the composition of the intestinal microflora.

It is proposed that this effect of the probiotic on the intestinal ecosystem impacts in some beneficial way on the consumer. A number of potential benefits arising from changes to the intestinal milieu through the agency of probiotics have been documented including: increased resistance to infectious diseases, particularly of the intestine, decreased duration of diarrhea, reduction in blood pressure, reduction in serum cholesterol concentration, reduction in allergy, stimulation of phagocytosis by peripheral blood leucocytes, modulation of cytokine gene expression, adjuvant effect, regression of tumors, and reduction in carcinogen or co-carcinogen production.

Christensen et al. was one of the first reporting that probiotic lactobacilli exerted their immunomodulatory effects by modulating the Th1/Th2/Th3/Tr1/Treg-promoting capacity of dendritic cells (DCs). They showed that when murine DCs were exposed to co-cultures of different *Lactobacillus* species, including *Lactoacillus reuteri*, they were differentially modulated for production of cytokines Il-6, IL-10, IL-12, and TNF-α, and for up-regulation of MHC class II and CD86 surface markers in a concentration dependent manner. All lactobacilli upregulated surface MHC class II and CD86 markers—indicative of DC maturation. Particularly notable in these studies was that *L. reuteri* (strain 12246) was a poor IL-12 inducer, but when co-cultured with *L. johnsonii* or *L. casei*, it differentially inhibited production of the proinflammatory cytokine signals IL-12, IL-6 and TNF-a, which were stimulated by the latter two species. IL-10 production remained unaltered under these conditions.

These findings led to their conclusions that "*L. reuteri* may contribute to an environmental modulation of the intestinal dendritic cell generation favoring tolerance toward antigens bearing no 'danger signal' while at the same time keeping intact the capacity to respond against pathogens recognized via a danger signal like LPS," that "*L. reuteri* might be a potential fine-targeted treatment effective for downregulating production of L-12 and TNF-α (and IL-6) while inducing the anti-inflammatory IL-10, thus representing an alternative therapeutic approach to counterbalance the pro-inflammatory intestinal cytokine milieu," and thus "the potential exists for Th1/Th2/Th3 driving capacities of the gut to be modulated according to composition of gut microflora, including ingested probiotics." (Christensen H R, Frokiaer H, Pestka J J (2002) Lactobacilli differentially modulate expression of cytokines and maturation surface markers in murine dendritic cells. J Immunol 168 171-178).

Smits et al. extended these observations and showed that *L. reuteri* has the ability to prime DCs to stimulate T regulatory (TR) cell production. They used three different *Lactobacillus* species co-cultured in vitro with human monocyte-derived DCs. Two of the lactobacilli, a human *L. reuteri* strain (ATCC 53609) and *L. casei*, but not a *L. plantarum* strain, primed these DCs to stimulate development of TR cells. These TR cells were shown to produce increased levels of IL-10 and were able to inhibit proliferation of bystander T cells in an IL-10-dependent fashion (Smits H H, Engering A, van der Kleij D, de Jong E C, Schipper K, van Capel T M M, Zaat B A J. Yazdanbakhsh M, Wierenga E A, van Kooyk Y, Kapsenberg L (2005) Selective probiotic bacteria induce IL-10-producing regulatory T cells in vitro by modulating dendritic cell function through dendritic cell-specific intercellular adhesion molecule 3-grabbing nonintegrin. J Allergy Clin Immunol 115 1260-1267).

One of the first pieces of evidence concerning an effect of orally administered *L. reuteri* on the host per se was an increased CD4+/CD8+ T cell ratio observed in the chick ileum (Walter J. Dobrogosz, NUTRAfoods 2005 4(2/3) 15-28). Valeur et al. recently extended this observation to include the human ileum. They obtained direct in situ evidence in human subjects showing (a) distribution of individual human-specific *L. reuteri* ATCC 55730 cells throughout the human gut and (b) apparent involvement of *L. reuteri* ATCC 55730 in the recruitment and/or proliferation of CD4+ T cells specifically in the ileal regions of the intestines. They concluded that "*L. reuteri* administrations elicited a recruitment of CD4+ T-helper cells to the human epithelium. This recruitment may be one factor in explaining the probiotic effect of this *L. reuteri* strain in man" (Valeur N, Engel P, Carbajal N, Connolly E, Ladefoged K (2004) Colonization and immunomodulation by *Lactobacillus reuteri* ATCC 55730 in the human gastrointestinal tract, Appl Environ Microbiol 70 1176-1181).

Toll like receptors (TLRs) recognize microbial motifs and activate a set of genes that lead to cytokine production. Traditionally, TLRs have been regarded as sensors of microbial infections, and their role is to induce an inflammatory response. However, the motifs recognized by TLRs are not unique to pathogens but are general motifs shared by entire classes of microorganisms, and it is not fully understood how the immune system differentiates between commensal and pathogenic bacteria via the TLRs. Recently, data have shown that TLRs, despite their role in induction of the inflammatory response, also play a role in maintaining intestinal homeostasis by recognizing the commensal microflora (Rakoff-Nahoum S, Paglino J, Eslami-Varzaneh F, Edberg S, Medzhitov R. Recognition of commensal microflora by toll-like receptors is required for intestinal homeostasis. Cell. 2004 Jul. 23; 118(2):229-41).

Strains of a wide variety of *Lactobacillus* species, including *L. reuteri* have been used in probiotic formulations. *L. reuteri* is one of the naturally occurring inhabitants of the gastrointestinal tract of animals, and is routinely found in the intestines of healthy animals, including humans. It is known to have antimicrobial activity. See, for example U.S. Pat. Nos. 5,439,678, 5,458,875, 5,534,253, 5,837,238, and 5,849,289. When *L. reuteri* cells are grown under anaerobic conditions in the presence of glycerol, they produce the antimicrobial substance known as β-hydroxy-propionaldehyde (3-HPA).

There is a clear and complex relationship between the intestinal immune system and the commensal flora. Recently it has been demonstrated that the luminal endogenous flora can initiate the key process of bacteria-induced innate and adaptive host response through the activation of toll-like receptors (TLRs) and NOD-receptors, located on the intestinal epithelial cells (Haller D, Jobin C. Interaction between resident luminal bacteria and the host: can a healthy relationship turn sour? J Pediatr Gastroenterol Nutr 2004; 38: 123-36. Rakoff-Naholm S, Paglino J, Eslami-Varzaneh F, Edberg S, Medzhitov R. Recognition of commensal microflora by Toll-like receptors is required for intestinal homeostasis. Cell 2004; 118: 229-241). In animal models, cytokines can initiate a hyper-reflex response of the enteric neuromusculature through neuro- and myo-immune interactions (Milla P J. Inflammatory cells and the regulation of gut motility. J Pediatr Gastroenterol Nutr 2004; 39: S750.).

In experimental and clinical studies it has been demonstrated that specific probiotic strains inhibit proliferation of the T cells and reduce secretion of both Th1 and Th2 cytokines while preferentially generating suppressive cytokines such as IL-10 and TGF-β (Rautava S, Kalliomaki M, Isolauri E. Probiotics during pregnancy and breast-feeding might confer immunomodulatory protection against atopic disease in the infants. J Allergy Clin Immunol 2002; 109: 119-121). Further, in human volunteers, *L. reuteri* colonizes the human gastrointestinal tract and is able to exert immunomodulatory activity, including recruitment of CD4+ T-helper cells at the human ileum epithelium (Valeur N, Engel P, Carbajal N, Connolly E, Ladefoged K. Colonization and immunomodulation by *Lactobacillus reuteri* ATCC 55730 in the human gastrointestinal tract. Appl Environ Microbiol 2004; 70: 1176-81). Maturation of DCs is the process that converts immature DCs to mature antigen presenting cells that migrate to lymph nodes. This process results in the loss of the powerful antigen uptake capacity that characterizes immature DC and in the upregulation of co-stimulatory molecule expression and of various cytokines (Mellman I, Steinman R M: Dendritic cells: specialized and regulated antigen processing machines. Cell 2001, 106:255-8. Banchereau J, Briere F, Caux C, Davoust J, Lebecque S, Liu Y J, Pulendran B, Palucka K: Immunobiology of dendritic cells. Annu Rev Immunol 2000, 18:767-811).

Known maturation protocols are based on the environment that DCs are believed to encounter after or during exposure to antigens. The best example of this approach is the use of monocyte-conditioned media (MCM). MCM is generated in vitro by culturing monocytes and then using the culture supernatant fluid as a source of maturation factors. The major components in MCM responsible for maturation are the pro-inflammatory cytokines interleukin-1 beta (IL-1β), IL-6 and TNF-α (Reddy A, Sapp M, Feldman M, Subklewe M, Bhardwaj N: A monocyte conditioned medium is more effective than defined cytokines in mediating the terminal maturation of human dendritic cells. Blood 1997, 90:3640-6.). Mature DCs produce a variety of cytokines, which stimulate and direct the T cell response. Two of these cytokines are IL-10 and IL-12. These cytokines have opposing effects on the direction of the induced T cell response: IL-12 induces a Th1 type response whereas IL-10 inhibits such response.

Thus, the activation state of APCs (antigen presenting cells), including DCs, determines the type and magnitude of the $CD4^+$T cell response. Resting APCs (including epithelial cells in the thymus) may promote the development of $CD4^+$ $CD25^+$TR cells. During infection by pathogens, recognition of microbial molecules by TLRs results in activation of APCs. The APCs then produce IL-6 and additional soluble factors that together override the suppressive effects of TR cells, allowing efficient generation of $T_E$ (T effector cells) cells against the pathogen. The dynamic equilibrium between resting and activated APCs will also be influenced by the actions of both TR and TE cells (FIG. 1).

Pessi et al. (2000) describe IL-10 generation in atopic children following oral *Lactobacillus rhamnosus* GG. But unlike the invention herein the study does not describe specifically strains with the ability of producing high amounts of IL-10, selected for their efficiency against motility disorders and colic (Pessi T, Sutas Y, Hurme M, Isolauri E. Interleukin-10 generation in atopic children following oral *Lactobacillus rhamnosus*. GG. Clin Exp Allergy. 2000 December; 30(12): 1804-8).

A study by Hermelijn et al. (2005) shows *L. reuteri* and *Lactobacillus casei*, but not *Lactobacillus plantarum*, priming monocyte-derived DCs to drive the development of TR cells. These TR cells produced increased levels of IL-10. Unlike the invention herein, the authors do not connect the IL-10 elevation to gut motility or colic. Even when it comes to strains, the authors mention two different bacterial species being efficient in increasing IL-10 levels. This is in contrast to the invention herein where it is showed that the probiotic to be most effective reducing colic has to be determined and selected at the strain level as the different strains of the same species have a different ability to be effective in increasing IL-10 levels.

At present there is no cure for colic. The current treatment paradigm for colic consists of either pharmacological and/or non-pharmacological methods, providing at best marginal reduction of symptoms. Typical therapeutic interventions for colic offered to parents fall within four categories, including, dietary, physical, behavioral and pharmacological. Dietary manipulations include professional advice on various feeding techniques, or the use of hypoallergenic milk, soy or lactose free formulas, and an early introduction to solids (Lothe, L., et al. cow's milk formula as a cause of infantile colic: a double-blind study. Pediatrics 1982; 70:7-10; Forsyth B W C. Colic and the effect of changing formulas: a double-blind multiple-crossover study. J Pediatr 1989; 115, 521-6; Treem, W R, et al. Evaluation of the effect of a fiber-enriched formula on infant colic. J Pediatr 1991; 119695-701). However, neither the use of soy formulas, or changes in feeding techniques works effectively for every case of colic. A review of the data studying these recommendations showed that use of hypoallergenic formulas, such as partially hydrolyzed or amino acid-based, may benefit only about 25% of infants (Lucassen, P L B J, et al. Infantile colic: crying time reduction with a whey hydrolysate: a double-blind, randomized placebo-controlled trial. Pediatrics 2000; 106:1349-54; Estep, D C, et al. Treatment of infant colic with amino acid-based infant formula: a preliminary study. Acta Paediatr 2000; 89:22-7).

Physical strategies for the management of colic include physical movement of body positions to alleviate gas production/reflux, carrying, swaddling, applying abdominal pressure, or massaging the baby. Other methods include creating a sense of distraction to minimize infant awareness of colic such as taking an infant for a car ride, use of a car ride simulator, crib vibrator, or infant swings (Lipton E L. Swaddling and child care practice: historical, cultural and experimental observations. Pediatrics 1965; 35:521-67; Byrne J M, Horowitz F D. Rocking as a soothing intervention: the influence of direction and type of movement. Infant Behav Dev 1981; 4:207-18).

Another approach is to play recordings of sounds that supposedly soothe the baby. However, there is evidence in the medical literature that these methods do not work (Parkin P C, Schwartz C J, Manuel B A. Randomized controlled trial of three interventions in the management of persistent crying of infancy. Pediatrics 1993; 92(2): 197-201). These strategies, at best, are only marginally effective in abatement of colic symptoms.

Recommendations for behavioral interventions for the treatment of colic are the most inconsistent therapies available. Some authors advocate increasing sensory stimulation, while others advocate decreasing such stimulation (Balon A J. Management of infantile colic. Amer Pham Physician 1997; 55:235-242; Lucassen P L B J, Assendelft W J J, Gubbels J W, van Eijk T M, van Geldrop W J, Effectiveness of treatments for infantile colic: systematic review. BMJ 1998; 316(5): 1563-9; and Carey W B, "Colic"—primary excessive crying as an infant-environmental interaction. Pediatr Clin North Am 1984; 31:993-1005). Other recommendations include early response to crying, or allowing the infant to cry, offering a pacifier, implementation of a routine feeding schedule, using eye contact and interactive playing.

Pharmacologic intervention for the treatment of colic has led to the use of prescription and non-prescription medications. Currently employed prescription medications include belladonna alkaloids and opiates (paregoric), which may provide relief, but are fraught with risks including extra pyramidal symptoms, respiratory depression, and constipation. For example, anticholinergic drugs, similar in their effect to atropine, such as, Hyoscyamine (LEVISINE®, or GASTROSED®) and Dicyclomine dilate pupils, increase heart rate, decrease production of saliva, relieve spasms of gastrointestinal and urinary tracts, as well as bronchi. Although the anticholinergic drugs are the only prescription medications on the U.S. market that consistently have been shown to effectively treat infantile colic, unfortunately, up to 5% of treated infants may develop side effects, including breathing difficulties, apnea, seizures, syncope, asphyxia, coma and muscular hypotonia (Williams J, Watkin-Jones R. Dicyclomine: worrying symptoms associated with its use in some small babies (BMJ 1984; 288:901; Myers J H, Moro-Sutherland D, Shook J E. Anticholinergic poisoning in colicky infants treated with hyoscyamine sulfate. Am J Emerg Med 1997; 15:532-5). In addition, several cases of death have been reported in infants taking dicyclomine (Garriott J C, Rodriguez R, Norton L E. Two cases of death involving dicyclomine in infants. Clinical Toxicol 1984; 22(5):455-462).

Non-prescription medications that have been reported as effective treatment for infantile colic include several sedative or sleep-inducing drugs, including supraphysiologic (high dose) diphenhydramine (BENADRYL®), phenobarbital, chloral hydrate, and even alcohol. However, there is the potential for serious side effects associated with several of these agents in children with respiratory disease, thus limiting their widespread use in treating colic (Balon A J. Management of infantile colic. Amer Pham Physician 1997; 55:235-242; Gurry D. Infantile colic. Australian Pham Phys 1994; 23(3):337-34632).

A safer non-prescription medication for treatment of colic has largely included the administration of simethicone or dimethylpolysiloxane, a non-absorbable, over-the-counter drug, which reduces the size of intestinal gas bubbles. Simethicone has a very safe profile and is frequently recommended, despite several studies demonstrating that effectiveness of simethicone on infantile colic is no better than placebo (Metcalf, T J, et al., Pediatrics 1994 July; 94(1):29-34. Sferra, T J, et al., Pediatr Clin North Am 1996 April; 43(2):489-510. Danielson, B. et al., Acta Paediatr Scand 1985 May; 74(3): 446-50. Colon, A R, et al., Am Fam Physician 1989 December; 40(6): 122-4.). As a result, the most common treatment for colic today is to simply wait for the baby to grow out of the condition.

Therefore, there currently is a need for safe and effective compounds and compositions and techniques that prove useful for treating colic in infants and young children. The compositions and methods of the present invention, respond to this need, providing product that can safely and effectively treat the symptoms associated with colic in infants. Patent application EP1364483A10 describes probiotics for treatment of gut-neuromuscular abnormalities, such as colic in babies. As a probiotic the applicants mention several different bacterial species. This is in contrast to the invention herein where the probiotic to be most effective reducing colic is a specific lactic acid bacteria strain selected to be effective in increasing IL-10 levels and not a whole bacterial species, as the inventors of the present invention has showed that there are substantial differences in stimulation IL-10 production between strains also of the same species.

In 2005 Savino demonstrated that supplementation with *L. reuteri* ATCC 55730 significantly improved colicky symptoms in breast-fed infants compared to the standard therapy with Simethicone within 7 days of treatment. The response rate to the treatment with *L. reuteri* was 95% while only 7% of infants responded to Simethicone. He presented results at the European Society for Pediatric Research (ESPR), Meeting Aug. 31, 2005-Sep. 3, 2005, Siena, Italy (*Pediatr Res*. 2005; 58(2): 411). Though Savino's results showed beneficial effects, he was not aware of the connection between certain strains promoting the production of IL-10 and the reduction of gut motility and consequently colic. The invention herein provides a method for selecting such best strains.

Collins described that disturbances of motor function produce a variety of symptoms that can arise in the context of inflammation or immune activation in various gut regions and embrace such common entities as esophagitis, gastritis, and idiopathic inflammatory bowel disease (IBD). These observations suggest that motility of the gut is also subject to the influence of the immune system. In this context, the motor system may play an important role in defending the gut against noxious stimuli present in the lumen (Collins S., The Immunomodulation of Enteric Neuromuscular Function Implications for Motility and Inflammatory Disorders. Gastroentrology 1996; 111: 1683-1699). This notion is reflected, for example, by the observation of Vantrappen et al., who showed that bacterial overgrowth in the small intestine is accompanied by disruption of the normal cyclic pattern of interdigestive motility in the small intestine (Vantrappen G, Jannssens J, Hellemans J, Ghoos A. The interdigestive motor complex of normal subjects and patients with bacterial overgrowth of the small intestine. J Clin Invest 1977; 9:1158-1168).

It has been well known for many years that elevated IL-10 levels suppress over-activated immune systems. It has also previously been demonstrated that gut motility is controlled by neurological signals, that are connected to the intestinal immune system and that colic is a consequence of increased gut motility, for example, due to bacterial overgrowth.

In industrialized countries, hygienic measures begin as early as the birthing process, which disrupts the neonates capacity to uptake the mother's gut microflora. As a consequence, different microflora are established in the infant. Instead of harboring for example *Escherichia coli* and Lactobacilli the newborns are more often colonized with *Staphylococcus aureus* and other skin bacteria.

The inventors of the present invention has made the unexpected finding that while over-growth of skin bacteria overactivates the baby's immune system, leading to over-activated gut motility and colic as a consequence, a higher number of specific gut bacteria, such as *L. reuteri* DSM 17938, with capacity of promoting IL-10 production, leads to maturation of the TR system i.e. proliferation of CD4+ CD25+TR cells. Up-regulation of CD4+CD25+ cells leads to calmed gut motility and consequently to beneficial effects on babies with colic.

On account of these findings, nonpathogenic bacterial strains were selected for IL-10 increasing properties, and surprisingly, this property of the strains were found to correlate with a decrease in infantile colic. The invention consequently refers to the use of *L. reuteri* DSM 17938 for the manufacture of a medicament for the prophylaxis and/or treatment of colic, and other strains selected the same way.

It is a further object of the invention to provide products containing said strains and for the administration to animals, including humans. Other objects and advantages will be more fully apparent from the following disclosure and appended claims.

SUMMARY OF THE INVENTION

The invention herein provides certain strains of lactic acid bacteria selected for their capability of promoting production of IL-10 and consequently proliferation of CD4+CD25+ TR cells, for prophylaxis and/or treatment of colic, a method of selecting such strains, and products containing such strains.

Other objects and features of the invention will be more fully apparent from the following disclosure and appended claims.

DETAILED DESCRIPTION OF THE INVENTION AND PREFERRED EMBODIMENTS THEREOF

Figure 1:
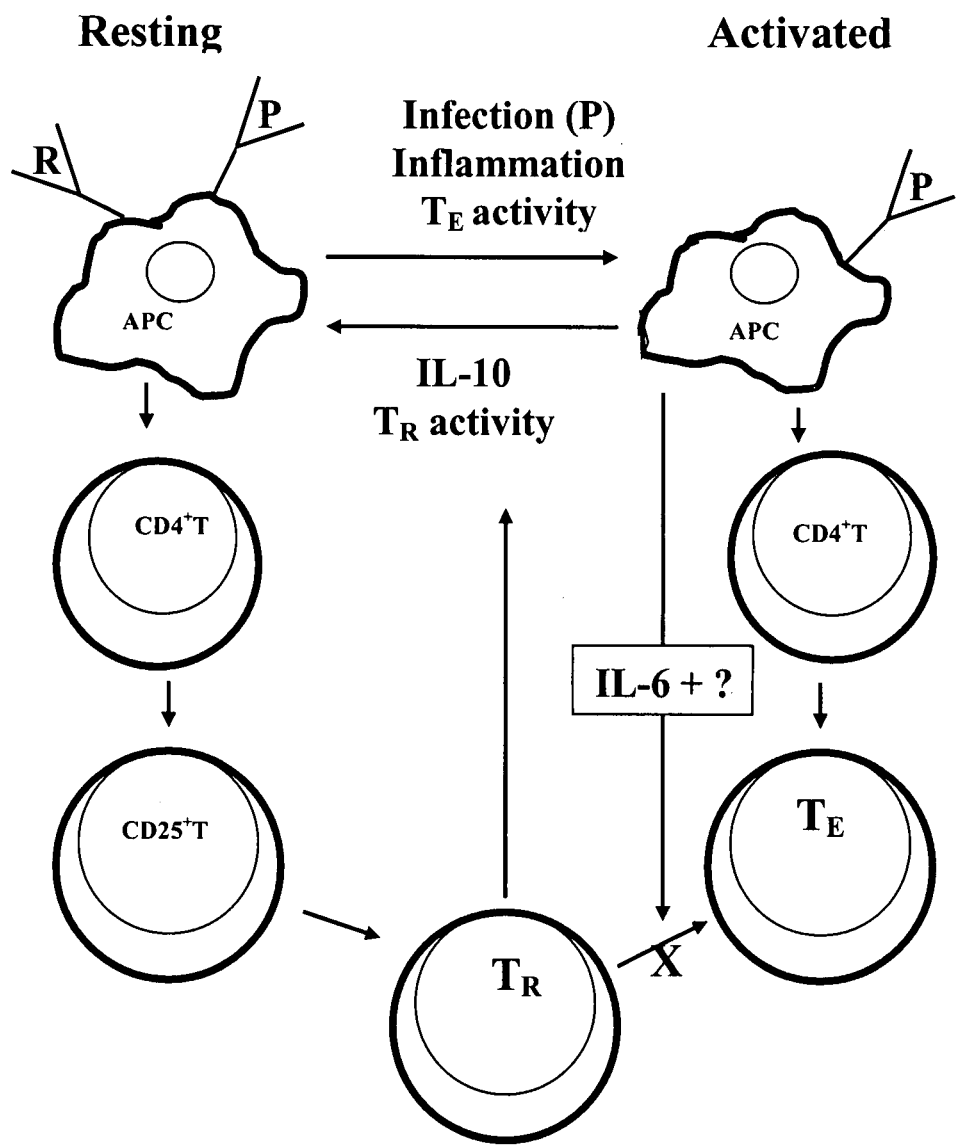
FIG. 1. Proposed role for certain selected lactic acid bacteria strains in promoting the development of $CD4^+CD25^+TR$ cells.

Colonization of skin bacteria in the gut and deficiency of TR-cells over-activate the immune system of the new-born baby, leading to over-activated gut motility and consequently colic. A larger number of specific gut bacteria cells, such as *L. reuteri* DSM 17938, with capacity of promoting IL-10 production, leads to maturation of the TR system i.e. proliferation of CD4+CD25+TR cells. Other lactobacilli strains have previously been reported by many researchers to induce production of L-10 for example Rautava et al (above). Up-regulation of CD4+CD25+ cells leads to calmed gut motility and consequently beneficial effects on colic. Surprisingly the strains that bring about an increase in cytokine IL-10 levels were found to be the same strains being able to decease the average crying time (EXAMPLE 2).

The present invention herein comprises strains of lactic acid bacteria which have been selected for their capability of reducing colic, including *L. reuteri* DSM 17938. Products such as foods, nutritional additives and formulations, pharmaceuticals or medical devices containing whole cells or components derived from these strains may be formulated as is known in the art, and generally include an ingestible support as known plus the *Lactobacillus*-strain, or its derived component.

An in vitro study may be used as a method for selecting strains of lactobacilli for their capability of stimulating the production of IL10 is monocyte-derived DCs and thereby capacity to induce the development of CD4+CD25+TR cells (Example 1).

Data disclose an indication of a powerful stimulation of IL-10 by the specific strains *L. reuteri* ATCC 55730 and *L. reuteri* DSM 17938, and that this regulation is mediated by a substance released into the growth medium by these two specific strains during late log/stationary growth phase. On the contrary, the two other strains of *L. reuteri* were unable to stimulate relevant IL-10 production.

To confirm the clinical relevance of the selected strains for preventing or treating colic further studies are performed in breast-fed infants with a diagnosis of infantile colic.

The features of the present invention will be more clearly understood by reference to the following examples, which are not to be construed as limiting the invention.

EXAMPLE 1

Study of probiotic strains ability to promote IL-10 expression by monocyte-derived DC:

Immature DCs are generated from peripheral blood monocytes (Hilkens, C. M. U., P. Kalinski, M. de Boer, and Kapsenberg. 1997. Human dendritic cells require exogenous interleukin-12-inducing factors to direct the development of naive T-helper cells toward the Th1 phenotype. Blood 90:1920) cultured in IMDM (Life Technologies, Paisley, U.K.) containing 10% FCS HyClone, Logan, Utah), recombinant human (rh)GM-CSF (500 U/ml; Schering-Plough, Uden, The Netherlands), and rhIL-4 (250 U/ml; Pharma Biotechnologie Hannover, Hannover, Germany) (Kalinski, P., J. H. N. Schuitemaker, C. M. U. Hilkens, E. A. Wierenga, and M. L. Kapsenberg. 1999. Final maturation of dendritic cells is associated with impaired responsiveness to IFN-γ and to bacterial IL-12 inducers: decreased ability of mature dendritic cells to produce IL-12 during the interaction with Th cells. J. Immunol. 162:3231).

Strains to be tested in this example are *Lactobacillus reuteri* ATCC 55730, *Lactobacillus reuteri* DSM 17938, *Lactobacillus reuteri* ATCC PTA 4660 and *Lactobacillus reuteri* ATCC PTA 4964 obtainable from ATCC (Manassas, Va., USA and DSMZ, Braunschweig, Germany). Strains are cultured on Columbia agar (Oxoid, Basingstoke, United Kingdom) containing 6.25% sheep blood. Lactobacilli are incubated at 37° C. in a 5% $CO_2$ atmosphere. After 3 days, the number of bacteria is determined by measuring the optical density at 620 nm (OD620). Typically, an OD620 of 0.35 corresponded to $1 \times 10^8$ colony-forming units (cfu) for all test strains.

On day 6, maturation of immature DCs is induced by LPS (*E. coli*; Sigma-Aldrich, St Louis, Mo.) and the test lactobacilli in the presence of the combination of the cytokines IL-1β (25 ng/mL) and TNF-α (50 ng/mL), together all used as maturation factors (cytokines purchased from Peprotech, Rocky Hill, N.J.).

Figures 2A, 2B:
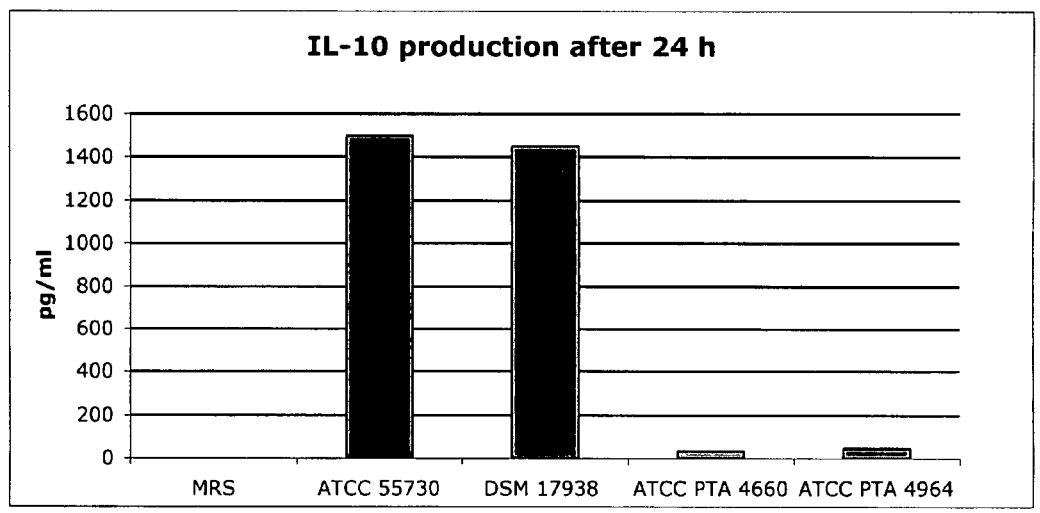
FIG. 2a. IL10 production by DC cells in bar-graph form.
FIG. 2b. IL10 production by DC cells in a table.

IL-12, IL-10, and IL-6 cytokine production by mature DCs is determined by means of a 24-hour stimulation with CD40 ligand-expressing mouse plasmacytoma cells (J558), as described by Vieira P L, et. al. (Vieira P L, de Jong E C, Wierenga E A, Kapsenberg M L, Kalinski P. Development of Th1-inducing capacity in myeloid dendritic cells requires environmental instruction. J Immunol 2000; 164:4507-12). Supernatants are harvested after 24 h, and the concentrations of IL-10 are measured by ELISA. For results see FIG. 2. As can be seen from the results, there is a substantial difference in influence by different *Lactobacillus* strains in their ability to promote IL-10 production by the DCs.

EXAMPLE 2

Selected Probiotic Strains Versus Simethicone in the Treatment of Infantile Colic Breast-fed infants with a diagnosis of infantile colic are recruited in the Department of Pediatric and Adolescence Science (Drottning Silvias University Hospital, Goteborg). Patients aged 21-90 days, adequate for gestational age with a birth weight between 2500 and 4000 g, with colic symptoms satisfying the Wessel's criteria, and arisen almost 6±1 days before the enrollment, are considered for inclusion in the study (Wessel M A, Cobb J C, Jackson E B, Harris G S, Detwiler A C. Paroxismal fussing in infancy, sometimes called "colic". Pediatrics 1954; 14: 421-35). All infants enrolled are exclusively breast-fed in order to reduce variability in the intestinal microflora due to variations in the diet, which may in turn have influenced the response to the probiotic. Infants are excluded if they had clinical evidence of chronic illness or gastrointestinal disorders or if they had received either antibiotics or probiotics in the week preceding recruitment.

In this study, colicky infants are randomized to receive the probiotic or Simethicone in the following treatments:
(P1) *Lactobacillus reuteri* strain ATCC 55730 also called SD2112,
(P2) *Lactobacillus reuteri* strain DSM 17938 (deposited at DSMZ-Deutsche Sammlung von Mikroorganismen und Zellkulturen GmbH (Mascheroder Weg 1b, D-38124 Braunschweig) on Feb. 6, 2006, under the Budapest Treaty)
(P3) *Lactobacillus reuteri* strain ATCC PTA 4660 and
(S) Simethicone All restrictions upon availability to the public of strain DSM 17938 will be irrevocably removed upon granting of the patent.

*L. reuteri* is administered at a dose of $10^8$ colony forming units (CFU) in 5 drops of a commercially available MCT-oil (medium chain tri-glyceride oil) suspension 30 min after feeding, once a day for 28 days. MCT oils occur naturally, and the most abundant source is coconut oil. Most MCT oil is refined from coconut oil. MCT oil is a clear light colored liquid with no flavor and low viscosity. This oil suspension is stable for 21 months at 2-8° C. (as documented by the manufacturer, BioGaia AB, Stockholm, Sweden) (alternative source of MCT oil is Akomed R, by Karlshamns AB, Karlshamn, Sweden). During the study, parents are instructed to keep the product in the refrigerator when not in use. Simethicone (S) was given at a dose of 60 mg/day in 3 mL of a commercially available solution (Mylicon Infants Gas Relief props, J&J, 7050 Camp Hill Rd., Fort Washington, Pa., 19034-2210, USA) after feeding, twice a day for 28 days. At the enrollment, all mothers are asked to follow a cows' milk-free diet as reported: avoidance of milk, yogurt, fresh and strong cheese, cream, butter, biscuits. Adherence to the diet is monitored with a diet diary maintained for all the treatment period. At day 7, 14, 21 and 28 one of the researches examined the compliance to this diet.

The Ethical Committee at the Institution approved the study protocol and infants are enrolled in the study only after written informed consent was obtained from the parents.

Follow-Up Visits

The day on which the pediatrician saw the infant for the first time is defined as Day −1. On this occasion each infant underwent a medical examination and the parents were interviewed in order to obtain background data concerning type of delivery, birth weight and gestational age, family history of gastrointestinal disease and atopy. In particular, the last one is considered positive if the infants had one or more family members (mother, father and/or older sibling) with atopic eczema, allergic rhinitis or asthma. Moreover, any signs and symptoms of atopic disease during the study period were recorded. Parents were also invited to record data concerning daily average crying time and number of colic episodes on the day after the recruitment (Day 0). The doctor randomly assigned the child to any of the study groups. Administration of study products began on Day 1.

Parents are given written information about the study and are asked to record daily number of inconsolable crying episodes and their duration, stool consistency and frequency as well as any observed side effects (constipation, vomiting, cutaneous reactions, etc) starting from Day 0 up to Day 28, using a structured diary. In order to ensure that all the parents noted crying time in a uniform way and to ensure that the infants are given the medication correctly, one of the researchers is always available by phone to help parents.

Each patient is re-examined by the same pediatrician on Days 1, 7, 14, 21 and 28.

Results

Of the 120 breast-fed colicky infants enrolled, 30 are randomly assigned to treatment with L. reuteri ATCC 55730 (P1), 30 are randomly assigned to treatment with L. reuteri DSM 17938 (P2), 30 are randomly assigned to treatment with L. reuteri ATCC PTA 4660 (P3) and 30 to Simethicone (S). No babies are withdrawn because of any side effect related to the trial. The groups are similar with respect to age, birth weight, gender, type of delivery, family history of atopy or gastrointestinal diseases, and exposure to smoking.

The average crying time per day is similar in the treatment groups on Day 0, and on Day 1. Infants receiving L. reuteri ATCC 55730 (P1) and DSM 17938 (P2) showed a significant reduction in daily crying time by Day 7 compared to infants treated with ATCC PTA 4660 and Simethicone(S). On Day 14, 21 and 28 crying time is significantly different between the four treatment groups. The difference between (P1) and (S) in average crying time per day from the beginning to the end of the study is 82 minutes, and the difference between (P2) and (S) in average crying time per day from the beginning to the end of the study is 83 minutes on Day 28 (Table 1). As can be seen from the results are the four treatment groups fairly even before the administration of the test products. Already after 7 days there is a clear difference in favor of L. reuteri strains ATCC 55730 and DSM 17938 over the two other alternatives. After 28 days the difference has grown larger.

TABLE 1

Crying time (mean minutes per day) in L. reuteri and Simethicone groups.

| Colicky infants N = 120 | L. reuteri ATCC55730 N = 30 | L. reuteri DSM 17938 N = 30 | L. reuteri ATCC PTA 4660 N = 30 | Simethicone N = 30 |
|---|---|---|---|---|
| Day 0 | 206 | 203 | 204 | 205 |
| Day 1 | 191 | 190 | 198 | 194 |
| Day 7 | 147 | 148 | 171 | 172 |
| Day 14 | 98 | 100 | 156 | 155 |
| Day 21 | 75 | 77 | 150 | 148 |
| Day 28 | 58 | 59 | 145 | 141 |

While the invention has been described with reference to specific embodiments, it will be appreciated that numerous variations, modifications, and embodiments are possible, and accordingly, all such variations, modifications, and embodiments are to be regarded as being within the spirit and scope of the invention.

What is claimed is:

1. A method of reducing infantile colic, comprising selecting a Lactobacillus reuteri strain capable of reducing gut motility in infants diagnosed with infantile colic by selecting a Lactobacillus reuteri strain capable of promoting IL-10 production by monocyte-derived dendritic cells after incubation with the strain, wherein promotion of IL-10 production leads to maturation of the TR system in the dendritic cells, and administering the selected Lactobacillus reuteri strain to infants diagnosed with infantile colic.

2. The method of claim 1, wherein the Lactobacillus reuteri strain is Lactobacillus reuteri strain DSM 17938.

3. A bacterial product for reducing infantile colic, consisting essentially of a biologically pure culture of the selected strain of Lactobacillus reuteri of claim 1, wherein the strain has been selected for use in reducing infantile colic by promotion of IL-10 production by monocite-derived dendritic cells after incubation with the strain, and wherein the strain of Lactobacillus reuteri is suspended in a liquid medium chain tri-glyceride oil.

4. The product of claim 3, wherein the Lactobacillus reuteri strain is Lactobacillus reuteri strain DSM 17938.

* * * * *